US012064327B2

(12) United States Patent
Su et al.

(10) Patent No.: US 12,064,327 B2
(45) Date of Patent: Aug. 20, 2024

(54) SHAPED FASTENING MEMBERS AND ABSORBENT ARTICLES HAVING THE SAME

(71) Applicant: The Procter & Gamble Company, Cincinnati, OH (US)

(72) Inventors: He Su, Beijing (CN); Koichi Morimoto, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 804 days.

(21) Appl. No.: 16/538,865

(22) Filed: Aug. 13, 2019

(65) Prior Publication Data

US 2020/0054505 A1 Feb. 20, 2020

(30) Foreign Application Priority Data

Aug. 14, 2018 (WO) .......................... CN2018/100423

(51) Int. Cl.
| | |
|---|---|
| *A61F 13/15* | (2006.01) |
| *A61F 13/56* | (2006.01) |
| *A61F 13/62* | (2006.01) |
| *A61F 13/58* | (2006.01) |

(52) U.S. Cl.
CPC ...... *A61F 13/5622* (2013.01); *A61F 13/5633* (2013.01); *A61F 13/622* (2013.01); *A61F 2013/587* (2013.01)

(58) Field of Classification Search
CPC .............. A61F 13/5622; A61F 13/5633; A61F 13/622; A61F 2013/587
See application file for complete search history.

(56) References Cited

U.S. PATENT DOCUMENTS

| | | |
|---|---|---|
| D132,937 S | 6/1942 | Cadgene |
| 3,658,064 A | 4/1972 | Pociluyko |
| 3,848,594 A | 11/1974 | Buell |
| 4,610,678 A | 9/1986 | Weisman |

(Continued)

FOREIGN PATENT DOCUMENTS

| | | |
|---|---|---|
| CN | 101346118 A | 1/2009 |
| CN | 101715336 A | 5/2010 |

(Continued)

OTHER PUBLICATIONS

Unpublished U.S. Appl. No. 16/684,860, filed Nov. 15, 2019, to Abhishek Prakash Surushe et al.

(Continued)

*Primary Examiner* — Jacqueline F Stephens
(74) *Attorney, Agent, or Firm* — William E. Gallagher; Sarah M. Decristofaro

(57) ABSTRACT

The present invention relates to a fastening member comprising a base pane, a closure member extending laterally from the base panel, the closure member comprising a closure member upper edge and a closure member lower edge, and a fastening element disposed on the closure member, the fastening element comprising a fastening element upper edge and a fastening element lower edge, wherein the closure member upper edge comprises a concave portion along the fastening element upper edge and the closure member lower edge comprises a convex portion along the fastening element lower edge, and wherein the closure member extends upwardly laterally.

5 Claims, 9 Drawing Sheets

(56) References Cited

U.S. PATENT DOCUMENTS

| | | | |
|---|---|---|---|
| 4,662,875 A | 5/1987 | Hirotsu |
| 4,673,402 A | 6/1987 | Weisman |
| 4,699,622 A | 10/1987 | Toussant |
| 4,808,178 A | 2/1989 | Aziz |
| 4,834,735 A | 5/1989 | Alemany |
| 4,834,741 A | 5/1989 | Sabee |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz |
| 3,860,003 B2 | 6/1990 | Buell |
| 4,946,527 A | 8/1990 | Battrell |
| 4,963,140 A | 10/1990 | Robertson |
| 4,990,147 A | 2/1991 | Freeland |
| 5,037,416 A | 8/1991 | Allen |
| 5,137,537 A | 8/1992 | Herron |
| 5,147,345 A | 9/1992 | Lavon |
| 5,151,092 A | 9/1992 | Buell |
| 5,156,793 A | 10/1992 | Buell |
| 5,167,897 A | 12/1992 | Weber et al. |
| 5,221,274 A | 6/1993 | Buell |
| 5,242,436 A | 9/1993 | Weil |
| 5,260,345 A | 11/1993 | Desmarais |
| 5,269,775 A | 12/1993 | Freeland |
| 5,342,338 A | 8/1994 | Roe |
| 5,387,207 A | 2/1995 | Dyer |
| 5,397,316 A | 3/1995 | Young |
| 5,499,978 A | 3/1996 | Buell |
| 5,507,736 A | 4/1996 | Clear |
| 5,549,592 A * | 8/1996 | Fries ............... A61F 13/58 |
| | | 604/389 |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,152 A | 1/1997 | Buell |
| D377,979 S | 2/1997 | Swenson et al. |
| 5,607,760 A | 3/1997 | Roe |
| 5,609,587 A | 3/1997 | Roe |
| 5,625,222 A | 4/1997 | Yoneda |
| 5,635,191 A | 6/1997 | Roe |
| 5,643,588 A | 7/1997 | Roe |
| D384,152 S | 9/1997 | Raufman |
| D403,400 S | 12/1998 | Dreier et al. |
| D403,401 S | 12/1998 | Dreier et al. |
| D403,402 S | 12/1998 | Dreier et al. |
| 5,851,205 A | 12/1998 | Hisada |
| 5,865,823 A | 2/1999 | Curro |
| 5,993,432 A | 11/1999 | Lodge |
| 6,004,306 A | 12/1999 | Robies |
| D428,142 S | 7/2000 | Stromblad |
| 6,107,537 A | 8/2000 | Elder |
| 6,120,487 A | 9/2000 | Ashton |
| 6,132,410 A | 10/2000 | Van Gompel et al. |
| D435,103 S | 12/2000 | Schmoker |
| 6,195,850 B1 | 3/2001 | Melbye et al. |
| 6,248,097 B1 | 6/2001 | Beitz |
| D448,079 S | 9/2001 | Bruemmer-prestley |
| 6,336,922 B1 | 1/2002 | Vangompel et al. |
| 6,410,129 B2 | 6/2002 | Zhang |
| 6,432,098 B1 | 8/2002 | Kline |
| 6,478,784 B1 | 11/2002 | Johnson |
| 6,677,258 B2 | 1/2004 | Carroll |
| 6,746,434 B2 | 6/2004 | Johnson |
| 6,843,134 B2 | 1/2005 | Anderson |
| 6,936,039 B2 | 8/2005 | Kline et al. |
| 6,945,968 B2 | 9/2005 | Svensson et al. |
| 7,062,983 B2 | 6/2006 | Anderson |
| D543,276 S | 5/2007 | Martynus et al. |
| D544,098 S | 6/2007 | Martynus et al. |
| 7,435,243 B2 | 10/2008 | Miyamoto |
| D581,525 S | 11/2008 | Zink et al. |
| D583,469 S | 12/2008 | Zink et al. |
| 7,626,073 B2 | 12/2009 | Catalan |
| 7,744,576 B2 | 6/2010 | Busam |
| 7,750,203 B2 | 7/2010 | Becker |
| 7,806,883 B2 | 10/2010 | Fossum |
| 7,819,853 B2 | 10/2010 | Desai |
| 7,867,213 B2 | 1/2011 | Bandorf et al. |
| 8,062,279 B2 | 11/2011 | Miyamoto |
| 8,145,338 B2 | 3/2012 | Kent |
| 8,145,343 B2 | 3/2012 | Debruler |
| 8,145,344 B2 | 3/2012 | Debruler |
| 8,227,071 B2 | 7/2012 | Wood et al. |
| 8,244,393 B2 | 8/2012 | Mclaughlin |
| 8,454,571 B2 | 6/2013 | Rezai |
| 8,618,350 B2 | 12/2013 | Mansfield |
| 8,712,573 B2 | 4/2014 | Debruler |
| 8,712,574 B2 | 4/2014 | Debruler |
| 8,784,722 B2 | 7/2014 | Rocha |
| 8,795,809 B2 | 8/2014 | Mansfield |
| 8,939,957 B2 | 1/2015 | Raycheck |
| 8,992,500 B2 | 3/2015 | Fujioka |
| 9,119,751 B2 | 9/2015 | Waksmundzki et al. |
| 9,138,362 B2 | 9/2015 | Popp |
| 9,265,673 B2 | 2/2016 | Stabelfeldt |
| 9,265,674 B2 | 2/2016 | Hancock-cooke |
| 9,301,889 B2 | 4/2016 | Miyamoto |
| 9,429,929 B2 | 8/2016 | Debruler |
| 9,468,265 B2 | 10/2016 | Horn |
| 9,468,569 B2 | 10/2016 | Hancock-cooke |
| 9,610,202 B2 | 4/2017 | Rezai et al. |
| 9,615,980 B2 | 4/2017 | Enz |
| 9,867,743 B2 | 1/2018 | Stabelfeldt |
| 9,980,859 B2 | 5/2018 | Popp |
| 10,034,802 B2 | 7/2018 | Macura et al. |
| D825,055 S | 8/2018 | Hirsch |
| 10,076,162 B2 | 9/2018 | Rocha |
| 10,085,897 B2 | 10/2018 | Landgrebe et al. |
| D879,972 S | 3/2020 | Caneppele et al. |
| D889,640 S | 7/2020 | Raycheck et al. |
| 10,798,997 B2 | 10/2020 | Rocha |
| 11,026,851 B2 | 6/2021 | Saito et al. |
| D928,310 S | 8/2021 | Chase et al. |
| D936,845 S | 11/2021 | Hahn et al. |
| 11,389,344 B2 | 7/2022 | Suyama |
| 11,399,990 B2 | 8/2022 | Suyama |
| 2002/0038110 A1 | 3/2002 | Kusibojoska et al. |
| 2002/0058923 A1 | 5/2002 | Suprise et al. |
| 2002/0193776 A1 | 12/2002 | Fernfors |
| 2003/0009144 A1 | 1/2003 | Tanzer et al. |
| 2003/0050616 A1 | 3/2003 | Reynolds et al. |
| 2003/0135192 A1 | 7/2003 | Guralski et al. |
| 2004/0082933 A1 | 4/2004 | Karami |
| 2004/0181200 A1 | 9/2004 | Desai |
| 2004/0193133 A1 | 9/2004 | Desai |
| 2005/0222552 A1 | 10/2005 | Otsubo |
| 2006/0129119 A1 | 6/2006 | Kistler |
| 2006/0178651 A1 | 8/2006 | Glaug |
| 2006/0212013 A1 | 9/2006 | Cohen et al. |
| 2006/0287637 A1* | 12/2006 | Lam ............... A61F 13/49015 |
| | | 604/389 |
| 2007/0000987 A1 | 1/2007 | Karlsson |
| 2007/0073260 A1 | 3/2007 | Roe |
| 2007/0219521 A1 | 9/2007 | Hird |
| 2007/0249254 A1 | 10/2007 | Mansfield |
| 2007/0287983 A1 | 12/2007 | Lodge |
| 2007/0293111 A1 | 12/2007 | Mansfield |
| 2009/0157034 A1 | 6/2009 | Mattingly et al. |
| 2009/0258210 A1 | 10/2009 | Iyad |
| 2009/0299323 A1 | 12/2009 | Schlinz et al. |
| 2010/0180407 A1 | 7/2010 | Rocha |
| 2011/0073513 A1 | 3/2011 | Weisman et al. |
| 2011/0092947 A1 | 4/2011 | Kline |
| 2011/0106043 A1* | 5/2011 | Waksmundzki .. A61F 13/15756 |
| | | 604/386 |
| 2011/0139657 A1 | 6/2011 | Hird |
| 2011/0139658 A1 | 6/2011 | Hird |
| 2011/0139659 A1 | 6/2011 | Hird |
| 2011/0152812 A1 | 6/2011 | Hird |
| 2011/0155304 A1 | 6/2011 | Sakaguchi |
| 2011/0178486 A1 | 7/2011 | Beck et al. |
| 2011/0184372 A1 | 7/2011 | Esping |

(56) References Cited

U.S. PATENT DOCUMENTS

| | | |
|---|---|---|
| 2011/0208144 A1 | 8/2011 | Roe et al. |
| 2012/0034413 A1* | 2/2012 | Miyamoto .......... A61F 13/5638 428/99 |
| 2012/0095429 A1 | 4/2012 | Kobayashi |
| 2012/0316526 A1 | 12/2012 | Rosati et al. |
| 2013/0082418 A1 | 4/2013 | Curro |
| 2013/0131625 A1 | 5/2013 | Schlinz |
| 2013/0226121 A1 | 8/2013 | Kikkawa et al. |
| 2013/0345657 A1 | 12/2013 | Nelson et al. |
| 2014/0000003 A1 | 1/2014 | Ashraf |
| 2014/0000070 A1 | 1/2014 | Ashraf |
| 2014/0000784 A1 | 1/2014 | Rane |
| 2014/0257227 A1 | 9/2014 | Roe |
| 2015/0032075 A1 | 1/2015 | Coenen et al. |
| 2015/0032079 A1 | 1/2015 | Enz et al. |
| 2015/0126955 A1 | 5/2015 | Sauer |
| 2015/0173963 A1 | 6/2015 | Coe et al. |
| 2016/0250085 A1 | 9/2016 | Lavon et al. |
| 2016/0270977 A1 | 9/2016 | Surushe |
| 2016/0278994 A1 | 9/2016 | Martynus et al. |
| 2017/0056253 A1 | 3/2017 | Chester et al. |
| 2017/0056256 A1 | 3/2017 | Smith |
| 2017/0287893 A1 | 10/2017 | Rouviere et al. |
| 2017/0326006 A1 | 11/2017 | Neubauer et al. |
| 2018/0042777 A1* | 2/2018 | Dalal ................ A61F 13/49058 |
| 2018/0042778 A1 | 2/2018 | Lenser |
| 2018/0050484 A1 | 2/2018 | Rocha |
| 2018/0228253 A1 | 8/2018 | Emslander et al. |
| 2018/0243147 A1 | 8/2018 | Swedberg et al. |
| 2018/0271716 A1 | 9/2018 | Dalal |
| 2018/0271717 A1 | 9/2018 | Dria |
| 2018/0325753 A1 | 11/2018 | Vohwinkel |
| 2019/0060135 A1 | 2/2019 | Kawka |
| 2020/0054505 A1* | 2/2020 | Su ...................... A61F 13/5622 |
| 2020/0113749 A1 | 4/2020 | Surushe et al. |
| 2020/0179184 A1 | 6/2020 | Kaiser |
| 2021/0145650 A1 | 5/2021 | Surushe et al. |
| 2021/0145660 A1 | 5/2021 | Surushe et al. |
| 2021/0145661 A1 | 5/2021 | Surushe et al. |
| 2021/0145662 A1 | 5/2021 | Hayden et al. |
| 2021/0145663 A1 | 5/2021 | Hayden et al. |
| 2021/0251824 A1 | 8/2021 | Roe |
| 2021/0386602 A1 | 12/2021 | Raycheck et al. |
| 2022/0257432 A1 | 8/2022 | Raycheck et al. |

FOREIGN PATENT DOCUMENTS

| | | | |
|---|---|---|---|
| CN | 102427786 A | 4/2012 | |
| CN | 103260569 A | 8/2013 | |
| CN | 104302261 A | 1/2015 | |
| CN | 104939979 A | 9/2015 | |
| CN | 105167917 A | 12/2015 | |
| CN | 105431122 A | 3/2016 | |
| CN | 105919731 A | 9/2016 | |
| CN | 206910449 U | 1/2018 | |
| EP | 1377214 B1 | 4/2005 | |
| EP | 2259763 B1 | 6/2014 | |
| JP | H11155906 A | 6/1999 | |
| JP | 2004508138 A | 3/2004 | |
| JP | 2006246999 A | 9/2006 | |
| JP | 2007521036 A | 8/2007 | |
| JP | 2009056001 A | 3/2009 | |
| JP | 2014138889 A | 7/2014 | |
| WO | 9108725 A | 6/1991 | |
| WO | WO9516746 A1 | 6/1995 | |
| WO | WO-0015069 A1 * | 3/2000 | ......... A44B 18/0061 |
| WO | 0156526 A1 | 8/2001 | |
| WO | WO 2005016211 A1 | 2/2005 | |
| WO | 2005110731 A2 | 11/2005 | |
| WO | 2011129097 A1 | 10/2011 | |
| WO | 2015015334 A1 | 2/2015 | |
| WO | 2016022629 A1 | 2/2016 | |
| WO | 2019018721 A1 | 1/2019 | |
| WO | 2019145647 A1 | 8/2019 | |
| WO | 2020041271 A1 | 2/2020 | |

OTHER PUBLICATIONS

Unpublished U.S. Appl. No. 16/684,895, filed Nov. 15, 2019, to Abhishek Prakash Surushe et al.
Unpublished U.S. Appl. No. 29/713,366, filed Nov. 15, 2019, to Abhishek Prakash Surushe et al.
All Office Actions; U.S. Appl. No. 16/684,860.
All Office Actions; U.S. Appl. No. 16/684,895.
All Office Actions; U.S. Appl. No. 29/713,366.
Case Search Report, PCT/CN2018/100423, dated May 15, 2019, 11 pages.
PCT Suppl. Search Report and Written Opinion for PCT/CN2018/100423 dated Apr. 28, 2020, 7 pages.
Definition for "integral," www.dictionary.com, Apr. 20, 2023, pp. 5.
"Commensurate", Merriam-Webster.com Dictionary, Merriam-Webster, Online retrieved from "https://www.merriam-webster.com/dictionary/commensurate. Accessed", No Known Date, 2 Pages.

* cited by examiner

SHAPED FASTENING MEMBERS AND ABSORBENT ARTICLES HAVING THE SAME

FIELD OF THE INVENTION

The present invention relates to fastening members having certain shapes, and absorbent articles having the fastening members.

BACKGROUND OF THE INVENTION

The use of fastening systems for securing the corners of disposable absorbent articles, such as diapers, has been known. Such systems are used to provide a secure means for keeping such articles on the wearer during use. They may also be used to provide a secure means for keeping such articles and their soiled contents wrapped up after use until disposal.

A typical fastening system for use with absorbent articles may have a fastening member and a landing member.

A fastening member is a critical component of absorbent articles. It controls the overall absorbent article position on a wearer, and contributes to the overall fit and wearer's comfort. The fastening member may be disposed directly or indirectly upon the longitudinal edge of the body portion in either the front or back of the absorbent article waist regions. In use, the fastening member may be secured to the landing member, which is disposed upon the correspondingly opposite body portion of the front or back of the absorbent article.

In conventional arrangement of fastening systems on absorbent articles, the fastening member comprise a base panel and a fastening element, and extends from a chassis in the direction parallel to the lateral direction of the absorbent article such that the fastening member is pulled in the lateral direction for fastening the article and for forming a defined dimension of the waist opening. This provides a lateral tensioning force to keep the absorbent article in the abdominal region of the wearer. The body of a wearer tends to push the article, or the article tends to be quite tight on the abdomen that the article can cause marks and irritation on the skin or cause discomfort to the wearer.

Fastening members have a tendency to neither distribute forces evenly within the base panel specially when the base panel is elastic, nor adequately provide sustained comfortable fit to the wearer.

Based on the foregoing, there is a need for a fastening member which provides an improved fit for wearer's body and comfort.

There is also a need for a fastening member which is able to be easily and inexpensively manufactured without creating a trim. None of the existing absorbent articles provides all of the advantages and benefits of the present invention.

SUMMARY OF THE INVENTION

The present invention relates to a fastening member comprising a base panel, a closure member extending laterally from the base panel, and a fastening element disposed on the closure member, wherein the fastening element comprises a fastening element upper edge and a fastening element lower edge, and the closure member comprises a closure member upper edge comprising a concave portion formed along the fastening element upper edge, a closure member lower edge comprising a convex portion formed along the fastening element lower edge, and a proximal portion extending upwardly laterally.

The present invention also relates to an absorbent article comprising a chassis; a first and a second opposing longitudinal side edges; a front waist region comprising a front waist edge and a back waist region comprising a back waist edge; and a fastening member, the fastening member comprising a base panel, a closure member extending laterally from the base panel, and a fastening element disposed on the closure member, wherein the closure member comprises a closure member upper edge comprising a concave portion, a closure member lower edge comprising a convex portion, and a proximal portion extending upwardly laterally. When the fastening member extends from the back waist region, it is disposed the closure member lower edge is located below the closure member upper edge with respect to the back waist edge. When the fastening member extends from the front waist region, it is disposed the closure member lower edge is located below the closure member upper edge with respect to the front waist edge.

BRIEF DESCRIPTION OF THE DRAWINGS

In the drawings, like numerals or other designations designate like features throughout the views.

DETAILED DESCRIPTION OF THE INVENTION

Figure 1:
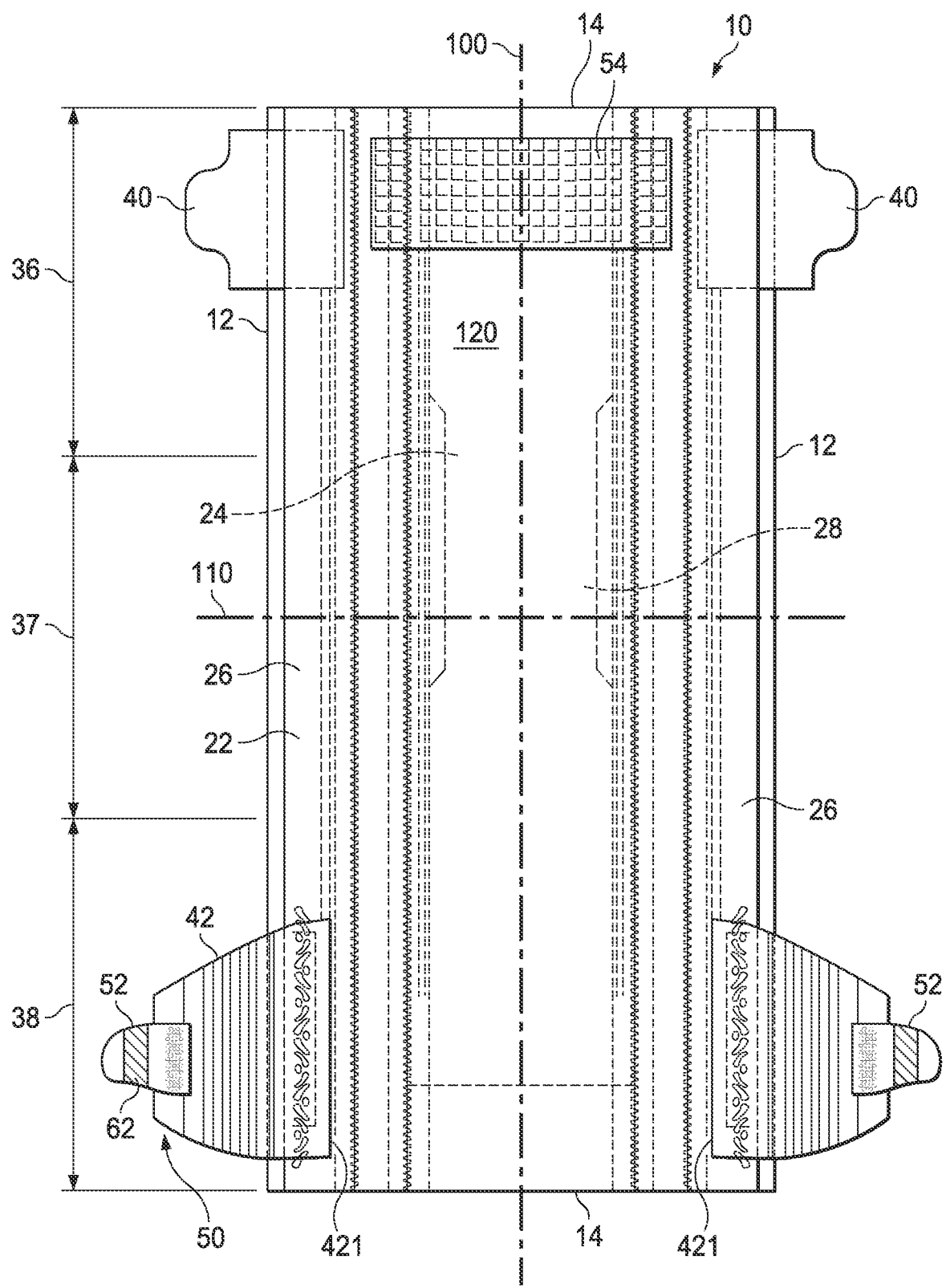
FIG. 1 is schematic plan view of an exemplary absorbent article according to the present invention.

Various non-limiting forms of the present disclosure will now be described to provide an overall understanding of the principles of the structure, function, manufacture, and use of an absorbent article comprising fastening members having unique shape. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the term "absorbent article" refers to disposable devices such as infant, child, or adult diapers, adult incontinence products, training pants, sanitary napkins and the like which are placed against or in proximity to a body of a wearer to absorb and contain the various fluids (urine, menses, and/or runny BM) or bodily exudates (generally solid BM) discharged from the body. Typically, these absorbent articles comprise a topsheet, backsheet, an absorbent core, leg cuffs, optionally an acquisition system and/or a distribution system (which may be comprised of one or several layers), and typically other components, with the absorbent core normally placed at least partially between the backsheet and the acquisition and/or distribution system or between the topsheet and the backsheet. The absorbent articles comprising a fastening member of the present invention will be further illustrated in the below description and in the Figures in the form of one or more components of taped diaper. Nothing in this description should be, however, considered limiting the scope of the claims. As such the present disclosure applies to any suitable form of absorbent articles (e.g., diapers, training pants, adult incontinence products, sanitary napkins).

"Elastic," and "elastomeric" mean the ability of a material to stretch by at least 25% without rupture or breakage at a given load, and upon release of the load the elastic material or component exhibits at least 80% recovery (i.e., has less than 20% set).

As used herein, the term "extensible" refers to the property of a material, wherein: when a force is applied to the material, the material can be extended to an elongated length of at least 110% of its original relaxed length (i.e. can extend 10%), without a rupture or breakage that renders the material unusable for its intended purpose. A material that does not meet this definition is considered inextensible. An extensible material may be able to be extended to an elongated length of 125% or more of its original relaxed length without rupture or breakage that renders the material unusable for its intended purpose. An extensible material may or may not exhibit recovery after application of a biasing force.

As used herein, the term "film" means a sheet-like material wherein the length and width of the material far exceed the thickness of the material (e.g., 10×, 50×, or even 1000× or more). Films are typically liquid impermeable but may be configured to be breathable.

As used herein, "inboard", and forms thereof, with respect to features of a fastening member, means furthest from or in a direction away from the free lateral distal end.

As used herein, the term "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "lateral" (and forms thereof), with respect to a line lying in a plane substantially occupied by an absorbent article fastening member laid flat and horizontally, viewed from above, relates to a direction substantially perpendicular to a longitudinal axis of the absorbent article. "Lateral" and "width" (and forms thereof), with respect to features of an absorbent article fastening member, relates to a direction, or generally following a direction, partially or entirely perpendicular to a longitudinal axis along the absorbent article. "Lateral" and "width" (and forms thereof), with respect to features of a diaper chassis, relates to a direction substantially parallel to the lateral axis of the chassis.

As used herein, the term "lateral axis" with respect to an absorbent article adapted to be worn by a wearer, means an axis perpendicular to the longitudinal axis, and equally dividing the longitudinal length of the article.

As used herein, the term "longitudinal" and "length" (and forms thereof), with respect to a line lying in a plane substantially occupied by an absorbent article fastening member laid flat and horizontally, viewed from above, relates to a direction approximately aligned with the wearer's spine when the article would be normally worn, with the wearer in a standing or extended reclining position. "Longitudinal" and "length" (and forms thereof), with respect to features of a fastening member, relates to a direction, or generally following a direction approximately aligned with the wearer's spine when the article would be normally worn, with the wearer in a standing or extended reclining position. "Longitudinal" and "length" (and forms thereof), with respect to features of a diaper chassis, relates to a direction approximately aligned with the wearer's spine when the article would be normally worn, with the wearer in a standing or extended reclining position.

As used herein, the term "longitudinal axis" with respect to an absorbent article adapted to be worn by a wearer, means an axis approximately aligned with the wearer's spine when the article would be normally worn, with the wearer in a standing or extended reclining position, and equally dividing the lateral width of the article.

As used herein, the term "nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

As used herein, the term "outboard", and forms thereof, with respect to features of a fastening member, means at or in a direction toward its free lateral distal end.

Where features or elements of claims set forth herein are identified as "lines" or "points", such lines or points are not actual physical features themselves unless otherwise specified, but rather, are geometric references intended for use in describing locations on a physical structure.

"Comprise," "comprising," and "comprises" are open ended terms, each specifies the presence of what follows, e.g., a component, but does not preclude the presence of other features, e.g., elements, steps, components known in the art, or disclosed herein.

"Machine direction" (MD) means the direction of material flow through a process. In addition, relative placement and movement of material can be described as flowing in the machine direction through a process from upstream in the process to downstream in the process. "Cross direction" (CD) means a direction that is generally perpendicular to the machine direction. "Z-direction," with respect to a web, means generally orthogonal or perpendicular to the plane approximated by the web along the machine and cross direction dimensions.

Absorbent Article

Chassis

FIG. 1 is a schematic plan view of a diaper 10, an example of absorbent articles according to the present invention, having a fastening member 50 of the present invention. The diaper 10 comprises a chassis 22 comprising a liquid pervious topsheet 24, a liquid impervious backsheet 26 and an absorbent core 28 disposed between the topsheet 24 and backsheet 26. The garment-facing surface 120 of the diaper 10 is facing the viewer. The diaper 10 includes a longitudinal centerline 100 and a lateral centerline 110. The diaper 10 includes a front waist region 36, a back waist region 38 opposed to the front waist region 36, and a crotch region 37 located between the front waist region 36 and the back waist region 38. The waist regions 36, 38 generally comprise those portions of the diaper 10 which, when worn, encircle the waist of the wearer. The waist regions 36 and 38 may include an elastic element that may gather or allow the material to extend in the front and/or back waist region 36, 38 about the waist of the wearer to provide improved fit and containment. The crotch region 37 is that portion of the diaper 10 which, when the diaper 10 is worn, is generally positioned between the legs of the wearer. The outer periphery of the diaper 10 is defined by longitudinal side edges 12 and end edges, i.e., front waist edge and back waist edge, 14. The opposing longitudinal side edges 12 may be oriented generally parallel to the longitudinal centerline 100. Elastic elements may be disposed adjacent the side edges 12 of the diaper 10 to form gasket cuffs when the diaper 10 is in a fastened configuration.

The diaper 10 shown in FIG. 1 includes a liquid permeable topsheet 24, a liquid impermeable backsheet 26, and an absorbent core 28 disposed therebetween. The absorbent core 28 may have a body-facing surface and a garment facing-surface. The topsheet 24, the backsheet 26, and the absorbent core 28 may be assembled in a variety of well-known configurations. For example, the topsheet 24 may be joined to the core 28 and/or the backsheet 26. The backsheet 26 may be joined to the core 28 and/or the topsheet 24. It should be recognized that other structures, elements, or substrates may also be positioned in a joined or unjoined relationship between the core 28, the topsheet 24 and/or the backsheet 26. Nonlimiting examples of suitable diaper configurations are described generally in U.S. Pat. Nos. 3,860,003; 4,808,178; 4,909,803; 5,151,092; 5,221,274; 5,554,145; 5,569,234; 5,580,411; 6,004,306; and 7,626,073; and U.S. Publication No. 2007/0249254A.

The topsheet 24 typically includes a portion of the diaper 10 that is positioned at least in partial contact or close proximity to a wearer. Suitable topsheets 24 may be manufactured from a wide range of materials, such as porous foams; reticulated foams; apertured films; or woven or nonwoven web of natural fibers (e.g., wood or cotton fibers), synthetic fibers, or a combination of natural and synthetic fibers; or multilayer laminates of these materials. Generally, at least a portion of the topsheet 24 is liquid pervious, permitting liquid to readily penetrate through the thickness of the topsheet 24. Any portion of the topsheet 24 may be coated with a lotion as is known in the art.

The absorbent core 28 may comprise a wide variety of liquid-absorbent materials commonly used in disposable diapers and other absorbent articles (e.g., superabsorbent polymer particles ("SAP") and/or airfelt). These materials may be combined to provide a core 28 in the form of one or more layers, which may include fluid handling layers such as acquisition layers, distribution layers and storage layers. Such absorbent cores 28 may also include layers such as a core cover layer to stabilize or confine other core components. The absorbent core 28 may include less than 20 wt % of airfelt, based on weight of the absorbent core 28, or the absorbent core 28 may even be airfelt-free. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222; 7,750,203; and 7,744,576.

The backsheet 26 may be positioned such that it includes at least a portion of the garment-facing surface 120 of the diaper 10. The backsheet 26 may be designed to prevent the exudates absorbed by and contained within the diaper 10 from soiling articles that may contact the diaper 10, such as bed sheets and undergarments. The backsheet 26 may be substantially water-impermeable. Suitable backsheet 26 materials may include breathable materials that permit vapors to escape from the diaper 10 while still preventing exudates from passing through the backsheet 26. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. Suitable materials and/or manufacturing techniques may be used to provide a suitable backsheet 26 including, but not limited to, surface treatments, particular film selections and processing, particular filament selections and processing, etc. The backsheet 26 may also include more than one layer configured, for example, as discrete, unjoined layers or as laminate. It is to be appreciated that such laminate structures are not limited to the backsheet 26, but may be incorporated into any of the diaper 10 components described herein or commonly known in the art (e.g., ears or sides panels), as desired. The diaper 10 may also include a fastening system. When fastened, the fastening system typically interconnects the front waist region 36 and the back waist region 38 resulting in a waist circumference that generally encircles a wearer of the diaper 10. Exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may be constructed to reduce shifting of overlapped portions or to improve fit as disclosed in U.S. Pat. Nos. 5,242,436; 5,499,978; 5,507,736; and 5,591,152.

Figure 2:
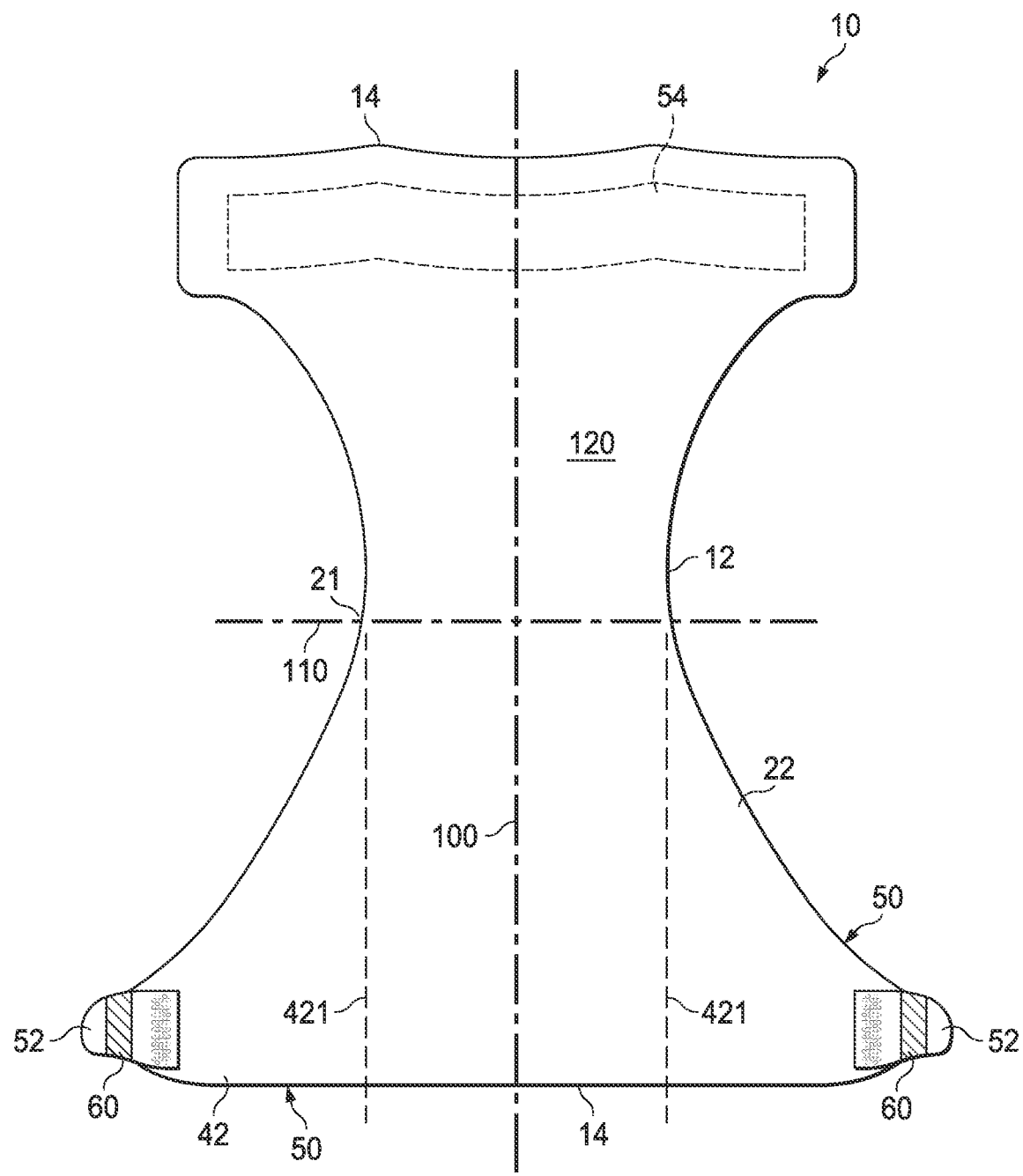
FIG. 2 is schematic plan view of another exemplary absorbent article according to the present invention.

The fastening system, as exemplified in FIGS. 1 and 2, may include a fastening member 50. The fastening member 50 may comprise a base panel 42 and a closure member 52, and be joined to any suitable portion of the diaper 10 by any suitable means. The fastening system may further comprise a landing zone 54 to which a fastening member 50 can engage and/or a release tape that protects the fastening element 62 from insult prior to use. Some exemplary fastening systems are disclosed in U.S. Pat. Nos. 3,848,594; 4,662,875; 4,846,815; 4,894,060; 4,946,527; 5,151,092; and 5,221,274. The closure member 52 is foldable.

FIG. 2 is a is schematic plan view of a diaper 10, an example of absorbent articles, having a fastening member 50 of the present invention when a base panel is not a discrete from, but rather, integral with, one or more components of a diaper chassis.

Fastening Member

A fastening member of the present invention comprises a base panel, a closure member extending laterally from the base panel, and a fastening element disposed on the closure member. The fastening element comprises a fastening element upper edge and a fastening element lower edge, and the closure member comprises a closure member upper edge comprising a concave portion formed along the fastening element upper edge, a closure member lower edge comprising a convex portion formed along the fastening element lower edge, and a proximal portion extending upwardly laterally.

The closure member may be joined to on an exterior surface of the base panel. The closure member may be joined to the base panel between layers consisting the base panel. The closure member may be mechanically bonded to the base panel.

Referring to FIGS. 1 and 2, a base panel 42 of the fastening member 50 extends laterally outwardly from one or both side edges 12 in the front and/or back waist regions. A base panel 42 may be a discrete component from other components of chassis of the diaper 10, and be joined to or overlapped with a chassis of a diaper 10, referring to FIG. 1. A base panel may be attached to an absorbent article in any suitable manner, including, but not limited to, continuous or intermittent adhesive bonding, compression bonding, heat bonding, ultrasonic bonding, etc. A base panel 42 may be integral with any of chassis component forming an extension thereof such that the base panel 42 may be configured as unitary elements of the backsheet, topsheet, core and/or another component in the chassis (i.e., they are formed from and are extensions of the backsheet, topsheet, core and/or the component materials). In such a case, when a fastening member 50 is disposed in an opened, extended position and laid flat and horizontally, viewed from above, referring to FIG. 2, the base panel inboard edge 421 means a line 421 parallel to the longitudinal axis 100 through the edge of the chassis 22 at its narrowest point 21.

Figure 3:
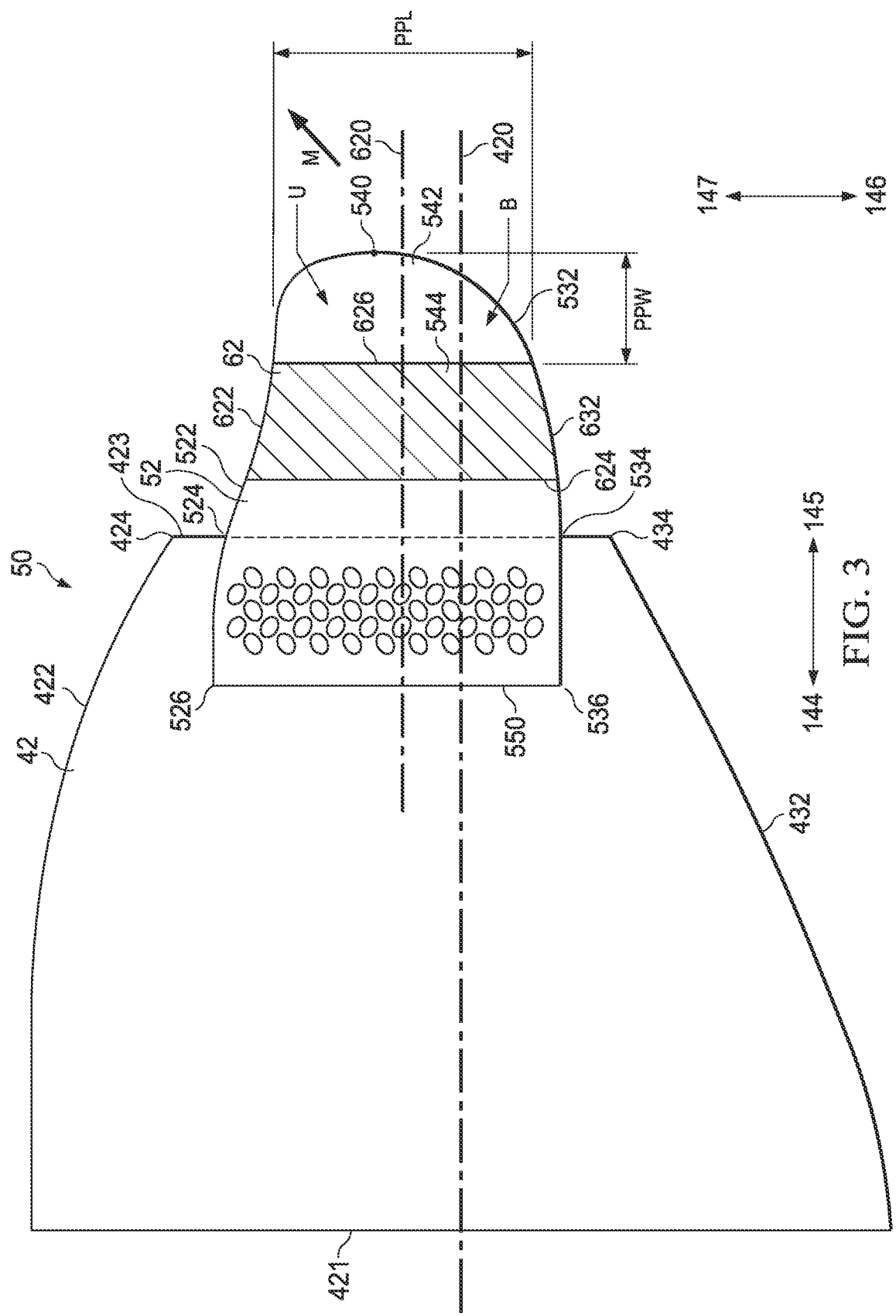
FIG. 3 is a schematic plan view of an exemplary fastening member according to the present invention.
Figure 4:
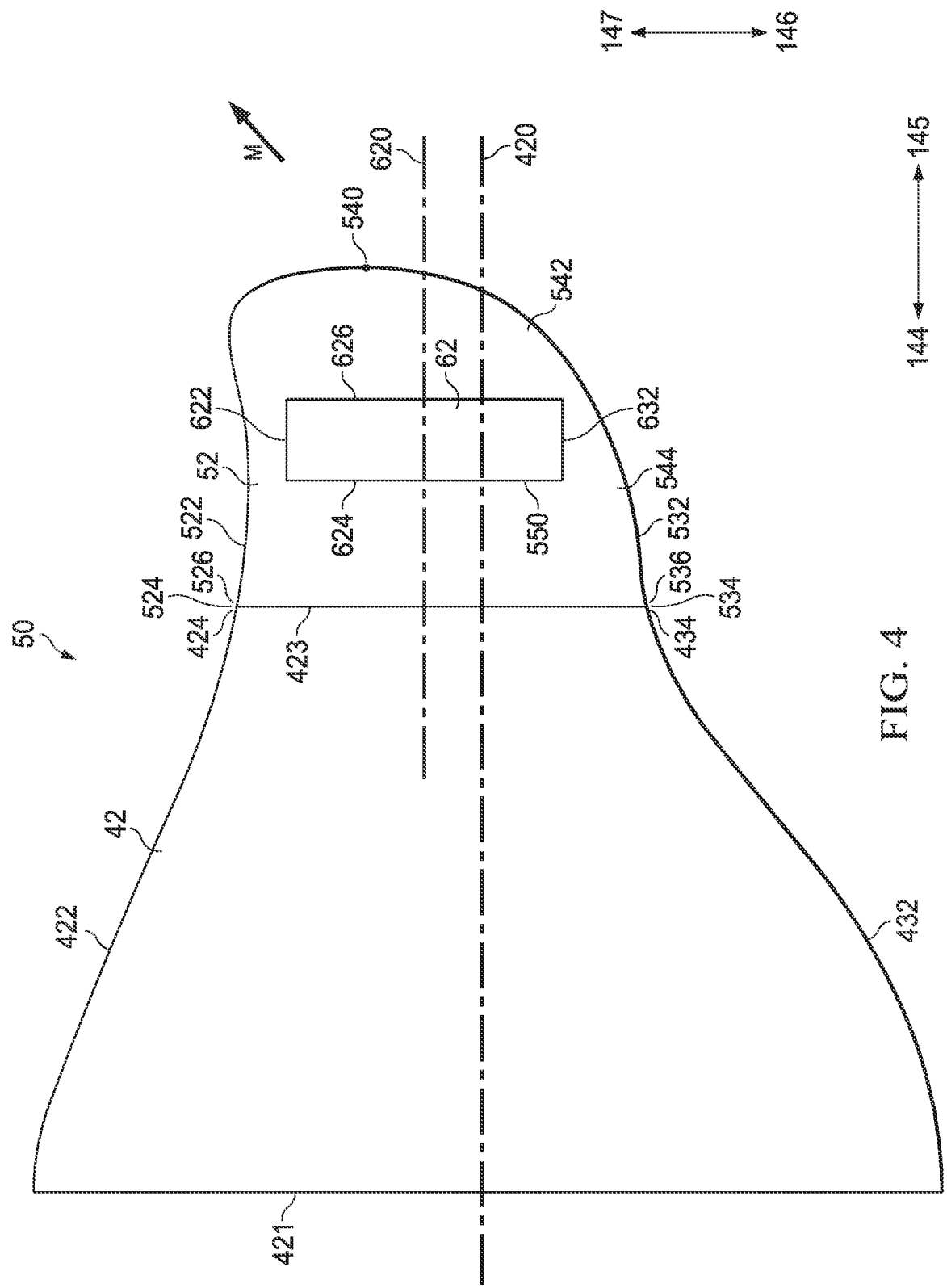
FIG. 4 is a schematic plan view of another exemplary fastening member according to the present invention.

Referring to FIGS. 3 and 4 showing exemplary fastening members of the present invention in a flat state, a base panel 42 has a base panel inboard edge 421 and a base panel outboard edge 423 which is substantially opposed to the inboard edge 421. The base panel 42 also has a base panel lateral centerline 420. A base panel lateral centerline 420 can be defined as an imaginary line extending in the longitudinal direction bisecting the base panel inboard edge 421.

A base panel may comprise any material such as a plastic film, woven or nonwoven webs of natural fibers (e.g., wood or cotton fibers), synthetic fibers (e.g., polyester or polypropylene fibers), or a combination of natural and synthetic fibers or may comprise any combination of materials thereof. A base panel is preferably compliant, soft feeling, and non-irritating to the wearer's skin as the base panel may touch the wearer's skin when in use. Further, at least a portion of the base panel may be vapor pervious, permitting vapor to readily penetrate through its thickness.

Any suitable nonwoven may be used for a base panel. Suitable nonwoven webs can be formed by direct extrusion processes during which the fibers and webs are formed at about the same point in time, or by preformed fibers which can be laid into webs at a distinctly subsequent point in time. Exemplary direct extrusion processes include but are not limited to: spunbonding, meltblowing, solvent spinning, electrospinning, and combinations thereof typically forming layers.

A base panel may include an elastomeric material, such that a least a portion of the base panel is extensible. A base panel may be formed of a stretch laminate such as a nonwoven/elastomeric material laminate or a nonwoven/elastomeric material/nonwoven laminate. A base panel may comprise a portion extensible laterally. The base panel may comprise a portion extensible longitudinally. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, elastic strands, scrims, and the like. Elastomeric materials can be formed from elastomeric polymers including polymers comprising styrene derivatives, polyesters, polyurethanes, polyether amides, polyolefins, polyvinyl chloride, combinations thereof or any suitable known elastomers. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, USA), HYTREL (polyester; available from DuPont, USA), VISTAMAXX (homopolyolefins and random copolymers, and blends of random copolymers, available from EXXON Mobile, USA), and VERSIFY (homopolyolefins and random copolymers, and blends of random copolymers, available from Dow Chemical Company, USA).

A fastening member of the present invention comprises a closure member and a fastening element disposed on the closure member.

A closure member may comprise the same material as the base panel. A closure member may comprise a material different from the material of a base panel which allows to provide the closure member with properties different from the base panel with respect to, e.g., stiffness and stretchability. The closure member may comprise a plastic film, a woven, a nonwoven or any combination thereof. The closure member may be stiffer than the base panel. The closure member may be less stretchable than the base panel. In an absorbent article having a fastening member of the present invention, the closure member which is stiffer and/or less stretchable than the base panel reduces to transmit the forces developed in the base panel therethrough in application or use of the absorbent article. It may also reduce to transmit the wrinkles created in the base panel due to the forces developed in the base panel.

Referring to FIGS. 3 and 4, the fastening member 50 comprises a base panel 42 and a closure member 52 extending laterally outwardly from the base panel 42. A closure member 52 extends laterally from the base panel 42, and comprises a closure member upper edge 522, a closure member lower edge 532, an upper junction point 524, a lower junction point 534, a closure member upper endpoint 526, a closure member lower endpoint 536, and a proximal portion 542.

Figure 5:
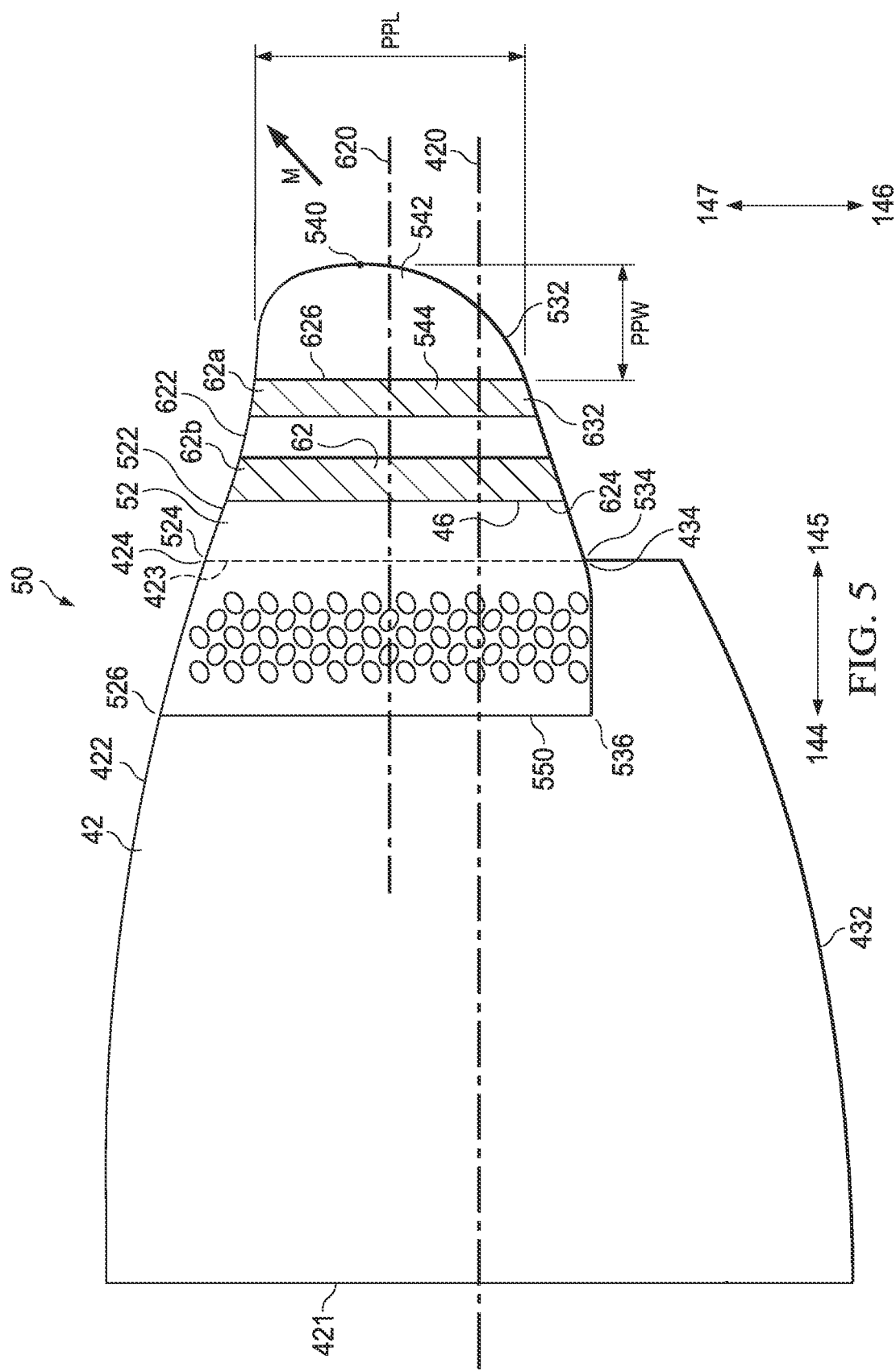
FIG. 5 is a schematic plan view of another exemplary fastening member according to the present invention.

A fastening element 62 comprises a fastening element lateral centerline 620, a fastening element upper edge 622, a fastening element lower edge 632, a fastening element inboard edge 624, and a fastening element outboard edge 626. A fastening element lateral centerline 620 can be defined as an imaginary line extending in the longitudinal direction bisecting the fastening element outboard edge 626. A fastening element in the present invention may have an irregular shape or orientation. In such examples, the longitudinal line passing a point at which such shape, orientation or engaging portions are farthest to a longitudinal axis of an absorbent article is considered a fastening element outboard edge, and the longitudinal line passing a point at which such shape, orientation or engaging portions are closest to a longitudinal axis of the absorbent article is considered a fastening element inboard edge. A fastening element may have a plurality of engaging portions, for example as shown in FIG. 5 where the fastening element 62 has two fastening portions, 62a and 62b.

A closure member 52 may be a discrete component from the base panel 42 and joined to the base panel 42 as exemplified in FIG. 3. The closure member 52 may be joined to the base panel 42 in any suitable manner, including, but not limited to, continuous or intermittent adhesive bonding, compression bonding, heat bonding, ultrasonic bonding, etc.

A closure member 52 may be integral with any of base panel materials (i.e., it is formed from and is an extension of any component material of the base panel). Referring to FIG. 4, when the closure member 52 is integral with the base panel 42 and is formed by the same material as the base panel 42, the base panel 42 and the closure member 52 can be sectioned by a base panel outboard edge 423 extending in the longitudinal direction as an imaginary line.

A closure member 52 has an outermost point 540. If a closure member 52 has a linear outermost edge in its lateral free distal end, a center point of the liner outermost edge is considered an outermost point 540. The closure member upper edge 522 between a closure member upper endpoint 526 and the outermost point 540 comprises a concave portion along a fastening element upper edge 622. The closure member lower edge 532 between a closure member lower endpoint 536 and the outermost point 540 comprises a convex portion along a fastening element lower edge 632. By "along a fastening element upper edge", it intends to mean that the concave portion in the closure member upper edge is formed along at least 80% or at least 90% of a fastening element upper edge. By "along a fastening element lower edge", it intends to mean that the convex portion in the closure member lower edge is formed along at least 80% or at least 90% of a fastening element lower edge.

A closure member upper edge having a concave portion along a fastening element upper edge can provide a better fit for the protruded belly of the wearer as it along with contour of the belly, and accommodate its significant protrusion. The concave portion helps cup the round underside of the protruding belly to reduce red-marking occurrence and improve comfort on the belly. The closure member lower edge having a convex portion may have a minimized area touching or rubbing legs of the wearer so that it may reduce red-marking and improve comfort on the skin. The concave portion in the closure member upper edge may also be effective to reduce transmission of a laterally pulling force created by a base panel or any part in the waist region into the closure member upper edge and help the laterally pulling force to concentrate into the center portion of the closure member. It may also effectively reduce wrinkles which are created in the base panel by the laterally pulling force, to be transmitted into the closure member upper edge, and helps the laterally pulling force to concentrate into the center portion of the closure member. Thus, as the laterally pulling force concentrates into the center portion of the closure member and the wrinkles are not transmitted into the closure member upper edge, the risk of unintended diaper opening due to closure member detachment can be reduced.

Still referring to FIGS. 3 and 4, the closure member upper edge 522 may comprise a continuous concave portion along the entire fastening element upper edge 622. The closure member lower edge 532 may comprise a continuous convex portion along the entire fastening element lower edge 632. The presence of the fastening element on the closure member may make the area where the fastening element is disposed stiffer, and skin irritation or red-makings becomes a more concerned problem. A fastening member according to the present invention having a closure member upper edge comprising a concave portion along the entire fastening element upper edge and a lower edge comprising a convex portion along the entire fastening element lower edge can resolve the concerned problem.

The concave portion in a closure member upper edge has slopes that are negative or zero, such that, the concave portion does not curve back up towards a wearer's belly. The convex portion in a closure member lower edge has slopes that are positive or zero. As used herein, the term "slope" refers to the rate of change between two points on the upper or lower edge of the closure member expressed as the difference in longitudinal location between the two points divided by the difference in lateral location between the two points. For the purpose of determining slope, FIGS. 3 and 4 are considered to be located in the first quadrant of a Cartesian coordinate system, where the laterally outboard direction 145 is the positive X direction and the longitudinally outboard direction 147 is the positive Y direction.

In the fastening member of the present invention, referring to FIGS. 3-5, the distance between a base panel upper endpoint 424 and an upper junction point 524 may be less than about 10 mm, or less than about 5 mm, or less than about 1 mm. The distance between a base panel upper endpoint 424 and an upper junction point 524 may be less than about 20%, or less than 10%, or less than 2% of base panel outboard edge 423.

The upper junction point 524 can be defined as points where the closure member upper edge 522 intersects a base panel outboard edge 423. For example, referring to FIGS. 4 and 5, a base panel upper edge 422 and a closure member upper edge 522 are substantially continuous and the distance between the base panel upper endpoint 424 and an upper junction point 524 is substantially zero. "Substantially zero" in this context intends to mean less than about 2 mm. The presence of multiple components in an absorbent article may not be favored by users in view of holistic product perception, and minimizing or even removal of a longitudinal gap between a base panel upper edge and a closure member upper edge may deliver users favorable perception of holistic integrated products.

In the fastening member of the present invention, referring to FIG. 3, the distance between the base panel lower endpoint 434 and a lower junction point 534 may be more than about 8 mm or more than about 10 mm. The distance between the base panel lower endpoint 434 and a lower junction point 534 may be more than about 16% or more than 20% of base panel outboard edge 423. Such a feature as specified above may be effective to reduce transmission of a laterally pulling force created by an elastic base panel or other elastic component in the waist region into the lower edge of the closure member and help the laterally pulling force to concentrate into the center portion of the closure member. Securing a longitudinal gap of at least about 8 mm between a base panel lower edge 432 and a closure member lower edge 532 also effectively reduces wrinkles which are created in the base panel 42 by the laterally pulling force, to be transmitted into the closure member lower edge 532, and helps the laterally pulling force to concentrate into the center portion of the closure member 52. Thus, as the wrinkles are not transmitted into the closure member lower edge, the risk of removal of the closure member 52 caused by the laterally pulling force transmitted to the closure member lower edge and the wrinkles can be reduced. Partial, if not entire, detachment of a closure member from a landing zone may result in falling off the absorbent article and leakage.

The closure member 52 shown in FIG. 3 has a proximal portion 542. The proximal portion 542, a portion of the closure member 52 from a fastening element outboard edge 626 to the outermost point 540, may serve as a grasp portion for the fastening member 50. The proximal portion 542 has a proximal portion width, ("PPW"), a width between the fastening element outboard edge 626 and the outermost point 540, and a proximal portion length ("PPL"). The fastening member 50 of the present invention may have a PPW in the range of about 6 mm-about 15 mm, or in the range of about 9 mm-14 mm. The fastening member 50 of the present invention may have a PPL in the range from about 18 mm to about 40 mm, or in the range of about 24 mm-30 mm A fastening member of the present invention having a closure member in dimensions aforementioned may provide users a grab area holing with a thumb finger and an index finger. If a PPW is too narrow and/or PPL is too short, it may not be easy for users to grab the fastening member sing two fingers. If the PPW is too wide and/or PPL is too long, the proximal portion may stand during wearing, and the fastening member may be easily open.

The fastening member of the present invention is designed to have a specific shape to provide directionality of the fastening member. Referring to FIGS. 3-5, the fastening member 50 of the present invention comprises a closure member 52 extending upwardly laterally. A fastening member designed to have such directionality also helps users engage the fastening member to a landing zone member close to a waist edge (waist circumference), so that more force is applied toward the belly providing improved fit and containment about the wearer's waist and less force is applied toward legs of a wearer with which wearer can feel improved comfort in leg areas.

The directionality of the fastening member 50 can be generally recognized by the shape of the proximal portion 542 of the shaped closure member 52. Referring to FIGS. 3 and 4, the proximal portion 542 of the shaped closure member 52 is designed to provide upwardness of directionality as indicated by the arrow M. When the proximal portion 542 of the closure member 52 extends upwardly laterally, the outermost point 540 of the closure member 52 is above a fastening element lateral centerline 620. Or, when the proximal portion 542 of the closure member 52 extends upwardly laterally, the fastening element lateral centerline 620 is located between the base panel upper edge 422 and the base panel lateral centerline 420. Or, the fastening element lateral centerline 620 intersects the closure member lower edge 532.

The fastening member of the present invention comprises a fastening element. Referring to FIGS. 1 and 2, a fastening element 62 is intended to provide a fastening means for engaging a landing zone or another portion of an absorbent article so as to provide a secure side closure for the absorbent article. A fastening element can be adhesives, hook and loop fastening components, interlocking fasteners such as tabs & slots, buckles, buttons, snaps, and/or hermaphroditic fastening components, although any other known fastening means are generally acceptable. The fastening element also may include groups of separately identifiable fastening components such as a plurality of discrete patches of adhesive-bearing material, discrete patches of hooks, etc. It should be understood that the use of the term "hook" should be non-limiting in the sense that the fastening components may comprise any shapes as are known in the art so long as they are adapted to engage a complementary landing zone member. The fastening element may comprise any of the well known configurations and securement means for achieving a side closure on a diaper.

Figure 6:
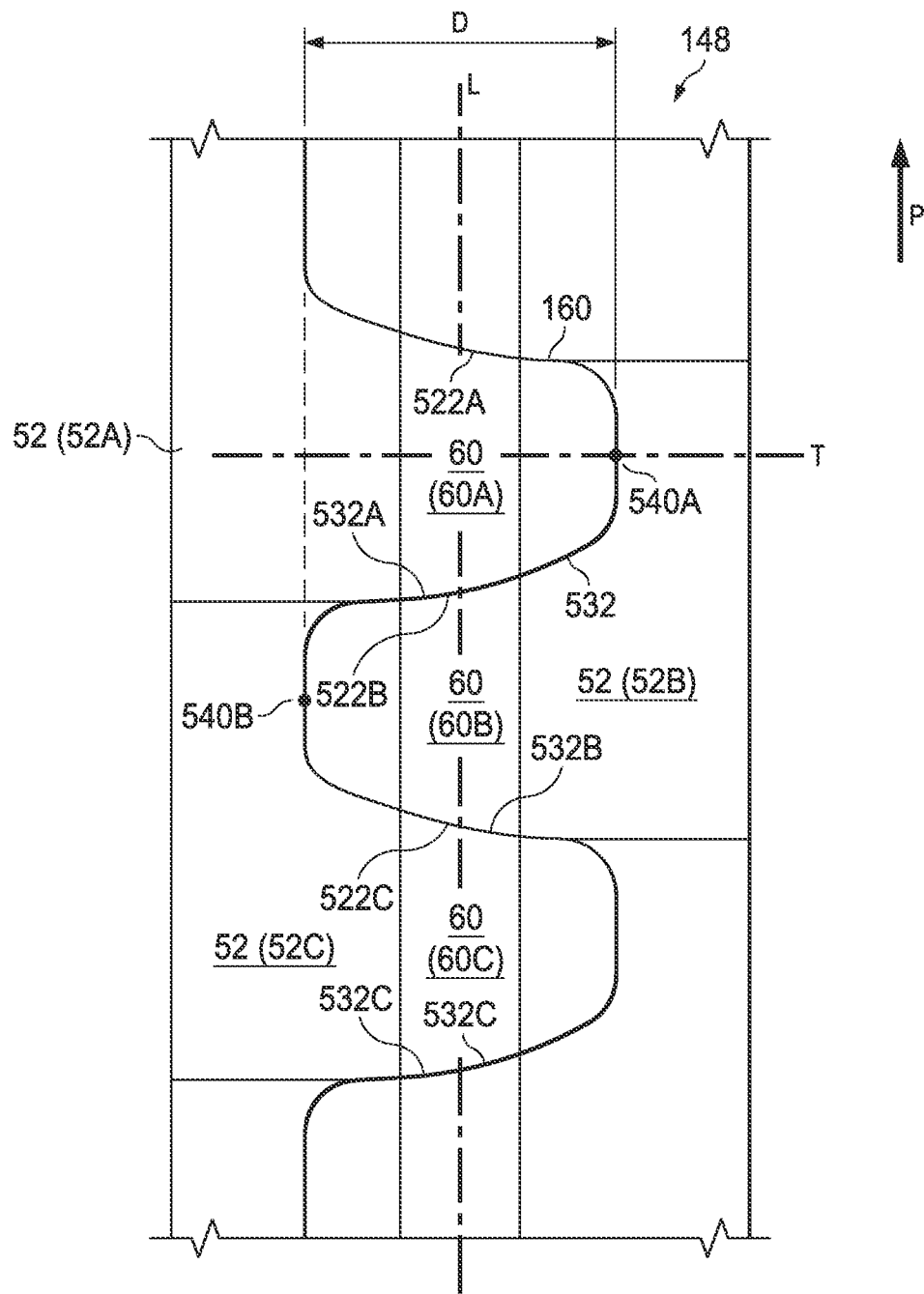
FIG. 6 is a schematic view of a process forming a plurality of closure members.

The fastening member of the present invention may have a closure member in a specific shape. The closure member upper edge 522 and closure member lower edge 532 have specific shapes. As shown in FIG. 6, the closure member upper edge 522 and the closure member lower edge 532 may be asymmetric with respect to a transversal line T intersecting the outermost point 540. The closure member upper edge 522 and the closure member lower edge 532 are symmetric with respect to a longitudinal line L when relatively shifted in the longitudinal direction. The longitudinal line L can be defined as a longitudinal line equally dividing a transversal length D determined by two outer most points, 540A and 540B.

The specific shapes of the closure member upper edge 522 and the closure member lower edge 532 are important to provide a closure member which is able to be easily and inexpensively manufactured without creating a trim. The asymmetry of the closure member upper edge 522 and the closure member lower edge 532 with respect to the lateral line T of the closure member 52 allows to provide the directionality of the shaped tab 51. The symmetricalness of the closure member upper edge 522 and the closure member lower edge 532 with respect to the longitudinal centerline L of the closure member 52 when relatively shifted in the longitudinal centerline L allows to continuously manufacture a fastening member easily and inexpensively without forming a trim.

FIG. 6 shows a schematic view of a process forming a plurality of closure members. In FIG. 6, closure member material 148 is provided in the direction indicated by the arrow P. The closure member material 148 has preferably been provided with a fastening element material such as a hook fastening material and/or adhesive material. The closure member material 148 is cut along a shaped cut line 160 generally extending in the longitudinal direction and cut along a cut line 162 to obtain a plurality of closure members 52. The cut line 162 forms the closure member lower edge 532A of the preceding closure member 52A and the closure member upper edge 522C of the following closure member 52C on the left side. In the embodiment shown in FIG. 6, the closure member 52B on the right side has the closure member upper edge 522B and the closure member lower edge 532B. The closure member upper edge 522B corresponds to the closure member lower edge 532A of the closure member 52A of the preceding closure member 52A on the left side. The closure member lower edge 532B corresponds to the closure member upper edge 522C of the following closure member 52C on the left side. Thus, the specific configuration of the fastening member allows to continuously manufacture a fastening member easily and inexpensively without forming any trim as well as providing directionality of the fastening member.

The present invention also provides an absorbent article comprising a chassis; a first and a second opposing longitudinal side edges; a front waist region comprising a front waist edge and a back waist region comprising a back waist edge; a fastening member extending in a longitudinal direction and in a lateral direction. The chassis comprises a liquid pervious topsheet, a liquid impervious backsheet, an absorbent core disposed between the liquid pervious topsheet and the liquid impervious backsheet; a first and a second opposing longitudinal side edges. The fastening member comprising: a base panel, a closure member extending laterally from the base panel, the closure member comprising a closure member upper edge and a closure member lower edge, and a fastening element disposed on the closure member, wherein the closure member upper edge comprises a concave portion, wherein the closure member lower edge comprises a convex portion, and wherein the closure member extends upwardly laterally. When the fastening member extends outwardly from the longitudinal side edge in the back waist region, it is disposed such that the closure member lower edge is located below the closure member upper edge with respect to the back waist edge. When the fastening member extends outwardly from the longitudinal side edge in the front waist region, it is disposed the closure member lower edge is located below the closure member upper edge with respect to the front waist edge.

The absorbent article according to the present invention may comprises a fastening member of the present invention disclosed in the specification.

EXAMPLES

Example 1: Diaper Preparation

Figure 7A:
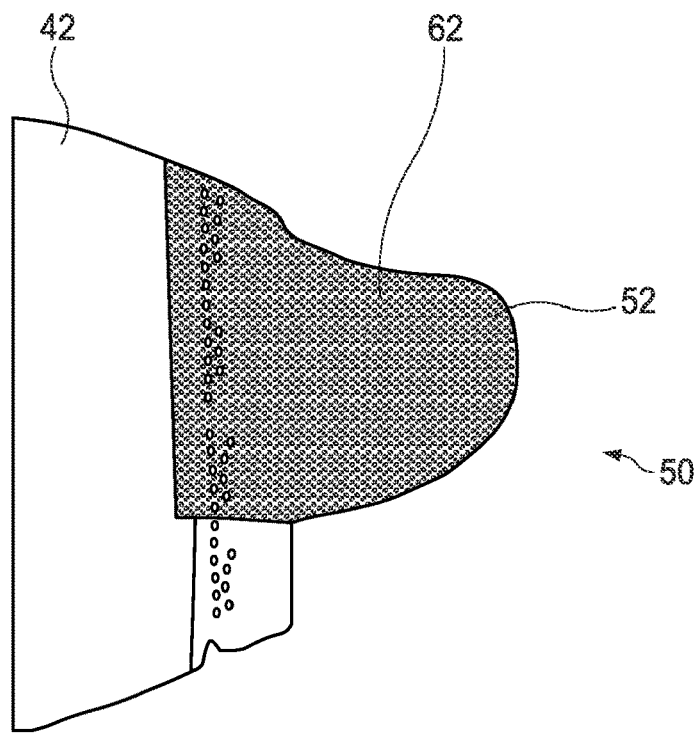
FIG. 7A is another exemplary fastening member according to the present invention.
Figure 7B:
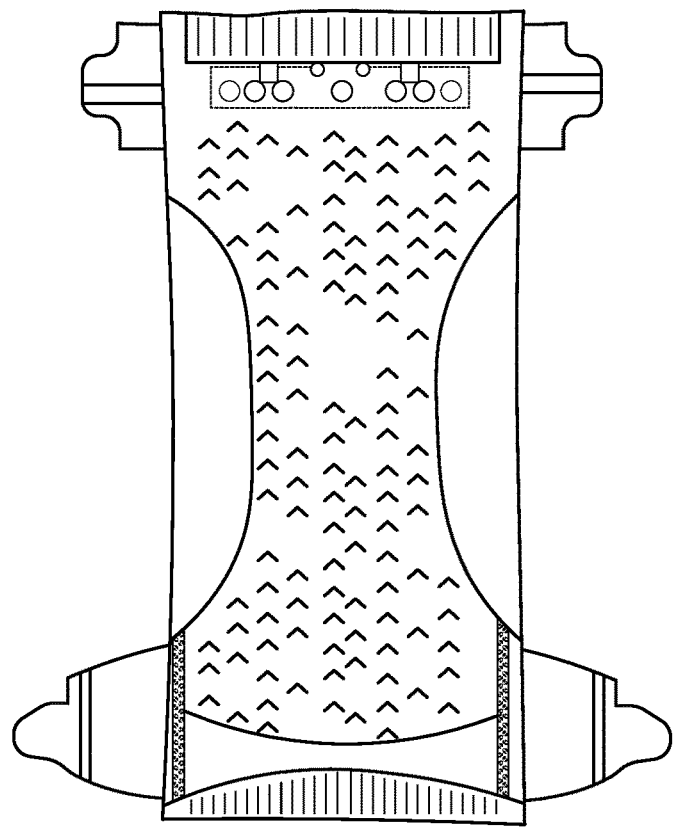
FIG. 7B is a top view from a garment facing side of an absorbent article having fastening members of FIG. 7A.
Figure 8A:
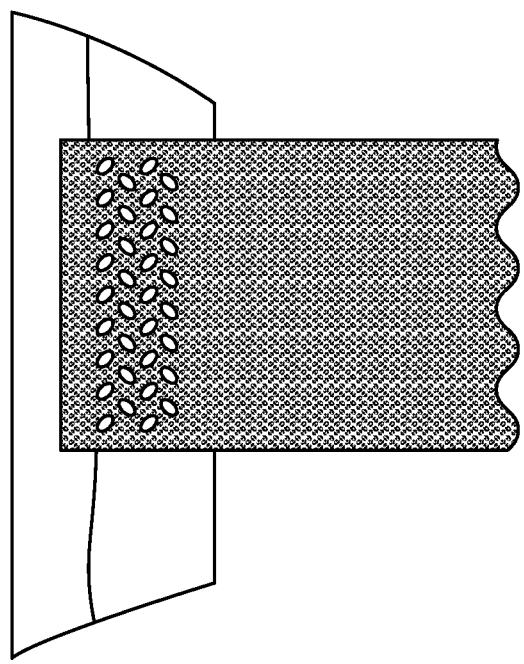
FIG. 8A is a comparative fastening member.
Figure 8B:
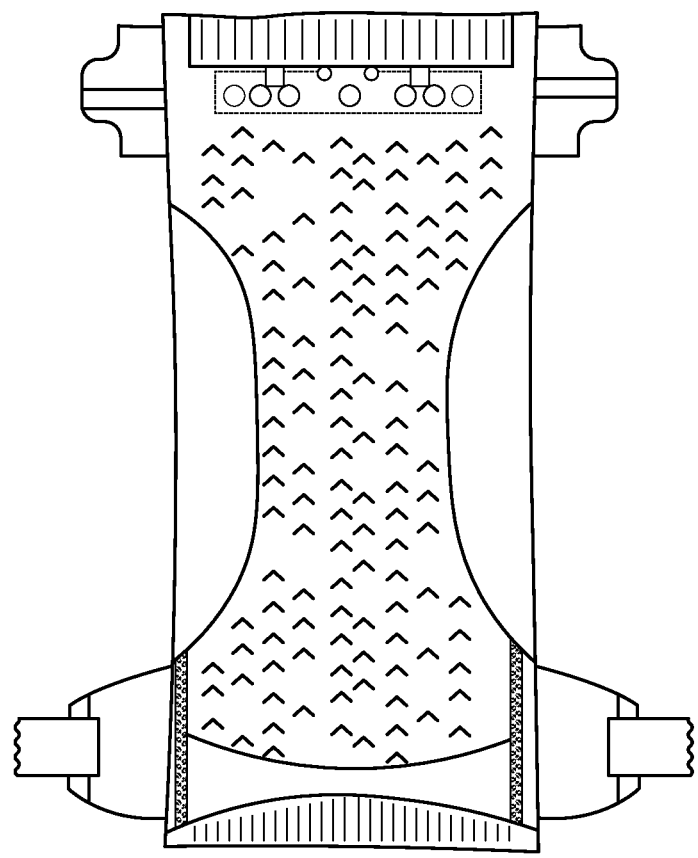
FIG. 8B is a top view from a garment facing side of an absorbent article having comparative fastening members of FIG. 8A.
Figure 9A:
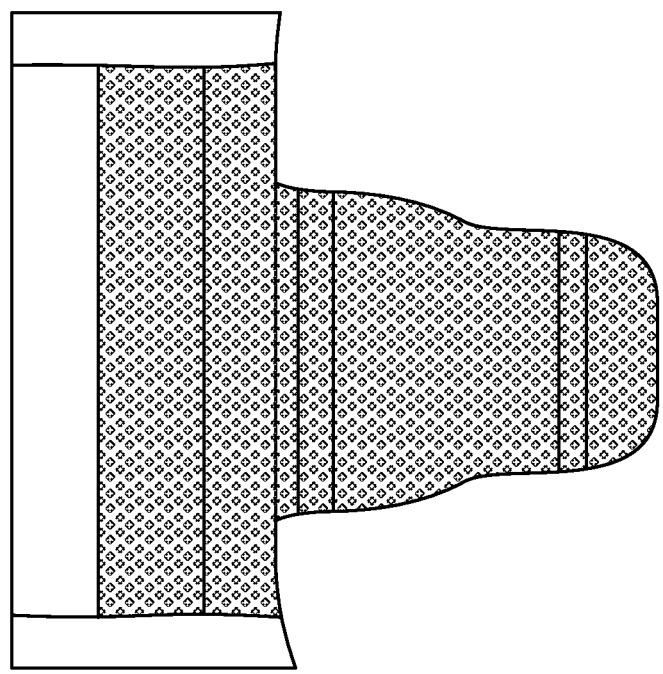
FIG. 9A is another comparative fastening member.
Figure 9B:
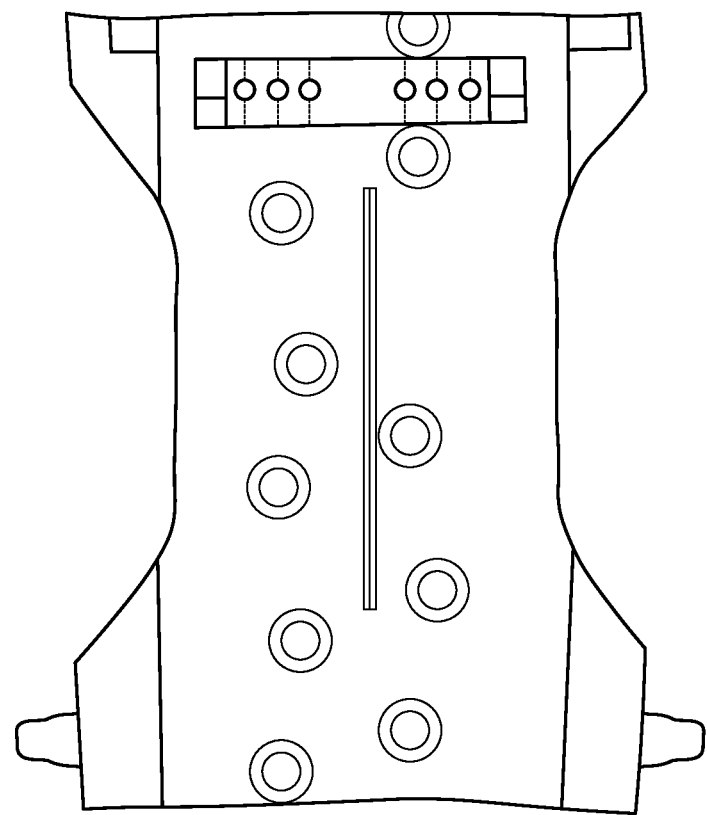
FIG. 9B is a top view from a garment facing side of an absorbent article having comparative fastening members of FIG. 9A.

A taped diaper (sample 1) of the present invention shown in FIG. 7B was prepared using Pampers Hajimeteno Hadaeno Ichiban (Procter and Gamble Japan K.K. Japan) by replacing closure members with closure members 52 of the fastening member 50 shown in FIG. 7A of the present invention. The closure member and fastening element materials in the fastening member 50 were identical to those in Pampers (P7.5), respectively. Pampers (P7.5) (Procter and Gamble Company, China) of FIG. 8B having fastening members shown in FIG. 8A and Merries Sarasara Airthrough (Kao Corporation, Japan) of FIG. 9B having fastening members shown in FIG. 9A were prepared as comparative samples 2 and 3, respectively.

Example 2

57 Chinese women with babies currently using L-size diapers were provided with sample 1 and comparative samples 1 and 2, all in size L, and requested to use each sample for 3 consecutive days and give each sample ratings for each item questioned. Ratings were provided with 5 rating scales (Poor (0), Fine (25), Good (50), Very good (75) and Excellent (100)). Results are shown in Table 1 below.

TABLE 1

| Question items | Sample 1 | Comparative sample 1 | Comparative sample 2 |
| --- | --- | --- | --- |
| Fit when first put on your baby | 75 | 70 | 71 |
| Has comfortable fasteners | 71 | 66 | 66 |
| Is easy to apply on | 74 | 71 | 71 |
| Conforms to baby's shape | 73 | 69 | 70 |
| Allows baby's belly to easily expand | 69 | 68 | 68 |
| Tape on Skin*[1] | 0.0% | 0.1% | 0.2% |

*[1](No. of pads with tape on skin/Total No. of pads used)

Example 3

55 Chinese women with babies currently using S-size diapers were provided with sample 1 and comparative samples 2 and 3, all in size S, and requested to use each sample for 3 consecutive days and give each sample ratings for each item questioned. Ratings were provided with 5 rating scales (Poor (0), Fine (25), Good (50), Very good (75) and Excellent (100)). Results are shown in Table 2 below.

TABLE 2

| Question items | Sample 1 | Comparative sample 1 | Comparative sample 2 |
| --- | --- | --- | --- |
| Fit when first put on your baby | 75 | 73 | 66 |
| Stays in place/fits the same as when I first put it on | 71 | 66 | 65 |
| Has comfortable fasteners | 75 | 71 | 66 |
| Is easy to apply on | 77 | 73 | 69 |
| Conforms to baby's shape | 70 | 66 | 66 |
| Allows baby's belly to easily expand | 70 | 70 | 61 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising
   a chassis comprising a liquid pervious topsheet, a liquid impervious backsheet, an absorbent core disposed between the liquid pervious topsheet and the liquid impervious backsheet;
   a first and a second opposing longitudinal side edges;
   a front waist region having a front waist edge and a back waist region having a back waist edge;
   a fastening member extending in a longitudinal direction and in a lateral direction in the back waist region, the fastening member comprising:
      a base panel,
      a closure member extending laterally from the base panel, the closure member comprising a closure member upper edge and a closure member lower edge, and
      a fastening element disposed on the closure member,
      wherein the closure member upper edge comprises a concave portion,
      wherein the closure member lower edge comprises a convex portion, and
      wherein the closure member extends upwardly laterally, wherein the fastening member is disposed in such a way that the closure member lower edge is located below the closure member upper edge with respect to the back waist edge, and wherein the closure member upper edge comprises a concave portion along the entire fastening element upper edge, and the closure member lower edge comprises a convex portion along the entire fastening element lower edge.

2. The absorbent article of claim 1, wherein the base panel is joined to the chassis.

3. The absorbent article of claim 1, wherein the base panel is integral with the chassis.

4. The absorbent article of claim 1, wherein the closure member is joined to the base panel.

5. The fastening member of claim 1, wherein the closure member is integral with the base panel.

* * * * *